United States Patent
Engelbart et al.

(10) Patent No.: US 8,668,793 B2
(45) Date of Patent: *Mar. 11, 2014

(54) SYSTEMS AND METHODS FOR IN-PROCESS VISION INSPECTION FOR AUTOMATED MACHINES

(75) Inventors: Roger W. Engelbart, St. Louis, MO (US); Reed E. Hannebaum, Belleville, IL (US); Timothy Pollock, Ballwin, MO (US)

(73) Assignee: The Boeing Company, Chicago, IL (US)

( * ) Notice: Subject to any disclaimer, the term of this patent is extended or adjusted under 35 U.S.C. 154(b) by 1889 days.

This patent is subject to a terminal disclaimer.

(21) Appl. No.: 11/202,411

(22) Filed: Aug. 11, 2005

(65) Prior Publication Data
US 2007/0034313 A1 Feb. 15, 2007

(51) Int. Cl.
*B32B 38/00* (2006.01)
*B32B 41/00* (2006.01)
*B32B 37/00* (2006.01)

(52) U.S. Cl.
USPC ............. 156/64; 156/379; 156/378; 156/361

(58) Field of Classification Search
USPC ................................ 165/64; 156/64, 378, 379
See application file for complete search history.

(56) References Cited

U.S. PATENT DOCUMENTS

| | | | |
|---|---|---|---|
| 4,672,678 A | 6/1987 | Koezuka et al. | |
| 4,699,683 A | 10/1987 | McCowin | |
| 4,706,296 A | 11/1987 | Pedotti et al. | |
| 4,790,023 A | 12/1988 | Matsui et al. | |
| 4,975,863 A | 12/1990 | Sistler et al. | |
| 5,012,523 A | 4/1991 | Kobayashi et al. | |
| 5,032,211 A | 7/1991 | Shinno et al. | |
| 5,231,675 A | 7/1993 | Sarr et al. | |
| 5,562,788 A * | 10/1996 | Kitson et al. ................ | 156/64 |
| 5,703,784 A | 12/1997 | Pearson | |

(Continued)

FOREIGN PATENT DOCUMENTS

| | | | |
|---|---|---|---|
| EP | 1334819 A1 | | 8/2003 |
| EP | 1503206 A1 * | | 2/2005 |
| EP | 1574845 A1 | | 9/2005 |

OTHER PUBLICATIONS

Assembly Guidance Systems website at http://www.assemblyguide.com/HAMPI/Hampi.htm, "Automatic Ply Verification", 2 pages, printed Oct. 17, 2005.

(Continued)

*Primary Examiner* — Michael Orlando
*Assistant Examiner* — Daniel Lee (57) ABSTRACT

Systems and methods for in-process vision inspection for automated machines are disclosed. In one embodiment, a head assembly includes a tool moveable over a workpiece and adapted to perform a manufacturing operation on the workpiece, and an inspection unit operatively positioned proximate the tool and moveable with the tool relative to the workpiece. The inspection unit is adapted to perform a vision inspection of a portion of the workpiece simultaneously with the performance of the manufacturing operation on the workpiece. In a particular embodiment, the inspection unit includes a camera adapted to monitor an area including the portion of the workpiece upon which the tool has performed the manufacturing operation, and a processor operatively coupled to the camera and adapted to receive an image from the camera and to analyze the image to determine a presence of a defect within the portion of the workpiece.

10 Claims, 10 Drawing Sheets

(56) References Cited

U.S. PATENT DOCUMENTS

| | | | |
|---|---|---|---|
| 5,742,504 | A | 4/1998 | Meyer et al. |
| 5,862,372 | A | 1/1999 | Morris et al. |
| 5,991,437 | A * | 11/1999 | Migdal et al. ............... 382/154 |
| 6,122,065 | A | 9/2000 | Gauthier |
| 6,381,366 | B1 | 4/2002 | Taycher et al. |
| 6,408,429 | B1 | 6/2002 | Marrion, Jr. et al. |
| 6,639,660 | B1 * | 10/2003 | Beck et al. ............... 356/237.2 |
| 6,723,951 | B1 | 4/2004 | McGraw |
| 6,744,913 | B1 | 6/2004 | Guest et al. |
| 6,799,619 | B2 | 10/2004 | Holmes et al. |
| 6,871,684 | B2 | 3/2005 | Engelbart et al. |
| 7,372,556 | B2 * | 5/2008 | Engelbart et al. ......... 356/237.1 |
| 7,407,556 | B2 * | 8/2008 | Oldani et al. ................ 156/64 |
| 2002/0141632 | A1 * | 10/2002 | Engelbart et al. ............. 382/141 |
| 2003/0102070 | A1 | 6/2003 | Black et al. |
| 2003/0210406 | A1 | 11/2003 | Hardy |
| 2004/0060650 | A1 | 4/2004 | Holmes et al. |
| 2006/0073309 | A1 | 4/2006 | Hogg |
| 2006/0108048 | A1 | 5/2006 | Engelbart et al. |
| 2007/0034313 | A1 | 2/2007 | Engelbart et al. |
| 2007/0097359 | A1 | 5/2007 | Engelbart et al. |

OTHER PUBLICATIONS

UltraOptec, Inc. website at http://www.ultraoptec.com/luis-747/LUIS-747.html, "Luis 747", 17 pages, printed Oct. 17, 2005.
PCT Intl Search Report and Written Opinion for Application No. PCT/US2006/031305, dated Nov. 14, 2006, 12 pages.

* cited by examiner

SYSTEMS AND METHODS FOR IN-PROCESS VISION INSPECTION FOR AUTOMATED MACHINES

FIELD OF THE INVENTION

This invention relates to systems and methods for visual inspection, and more specifically, to systems and methods for in-process vision inspection for automated machines, including automated multi-head composite tape placement machines and the like.

BACKGROUND OF THE INVENTION

Composite structures are commonly manufactured by progressively building up the structure with a plurality of layers of thin composite tape (or tow) laid one layer upon another. Typically, the operation begins by laying one or more tapes onto a starting template or tool that has a configuration generally corresponding to the desired shape of the article to be produced. A tape placement head of a manufacturing system moves over the surface of the template, guiding the one or more tapes of composite material onto the template. The head usually makes repeated passes over the template in a defined pattern until the composite material is entirely collated, building up successive layers of the composite tape to form the desired workpiece. A compaction roller is typically used for pressing the tape against the workpiece, thereby facilitating adhesion of the successive layers. The workpiece may then be subjected to a curing process (e.g. heating) to further adhere and bond the composite layers. Conventional systems for forming composite structures using successive layers of tape include those systems disclosed, for example, in U.S. Pat. No. 6,799,619 B2 issued to Holmes et al., and U.S. Pat. No. 6,871,684 B2 issued to Engelbart et al.

Although desirable results have been achieved using such prior art systems, there may be room for improvement. For example, inspections to ensure the quality of the composite components manufactured using the above-described systems may require downtimes which reduce the production rate and efficiency, and increase the overall cost, of the manufacturing process. Novel systems and methods which reduce or eliminate the downtime associated with inspections during the manufacture of composite components would therefore have utility.

SUMMARY OF THE INVENTION

The present invention is directed to systems and methods for in-process vision inspection for automated machines. Embodiments of systems and methods in accordance with the present invention may advantageously perform in-process inspections simultaneously on different regions of a workpiece, and may reduce downtime and associated costs, in comparison with the prior art.

In one embodiment, a head assembly adapted to perform a manufacturing operation on a workpiece includes a tool moveable over the workpiece and adapted to perform the manufacturing operation on the workpiece, and an inspection unit. The inspection unit is operatively positioned proximate the tool and moveable with the tool relative to the workpiece. The inspection unit is adapted to perform a vision inspection of a portion of the workpiece upon which the tool has performed the manufacturing operation simultaneously with the performance of the manufacturing operation on the workpiece. In a particular embodiment, the inspection unit includes a camera adapted to monitor an area at least partially including the portion of the workpiece upon which the tool has performed the manufacturing operation, and a processor operatively coupled to the camera and adapted to receive an image from the camera and to analyze the image to determine a presence of a defect within the portion of the workpiece. In alternate embodiments, the vision inspection includes a defect detection process including at least one of a striping process and an illumination process.

BRIEF DESCRIPTION OF THE DRAWINGS

Embodiments of the present invention are described in detail below with reference to the following drawings.

DETAILED DESCRIPTION

The present invention relates to systems and methods for in-process vision inspection for automated machines, including automated multi-head composite tape placement machines and the like. Many specific details of certain embodiments of the invention are set forth in the following description and in FIGS. 1-14 to provide a thorough understanding of such embodiments. The present invention may have additional embodiments, or may be practiced without one or more of the details described below.

Generally, embodiments of systems and methods in accordance with the present invention provide a vision unit operatively coupled with a head assembly adapted to perform a desired manufacturing operation, such as applying a fiber-reinforced composite tape onto a template to form a composite laminate workpiece. The vision unit advantageously performs visual inspections of the manufacturing operation during the performance of the manufacturing operation by the head assembly. Thus, embodiments of the invention advantageously reduce the labor and expense associated with performing inspections during manufacturing operations, including the manufacture of composite components, improving the production rate and efficiency, and reducing cost, in comparison with the prior art systems and methods.

Figure 1:
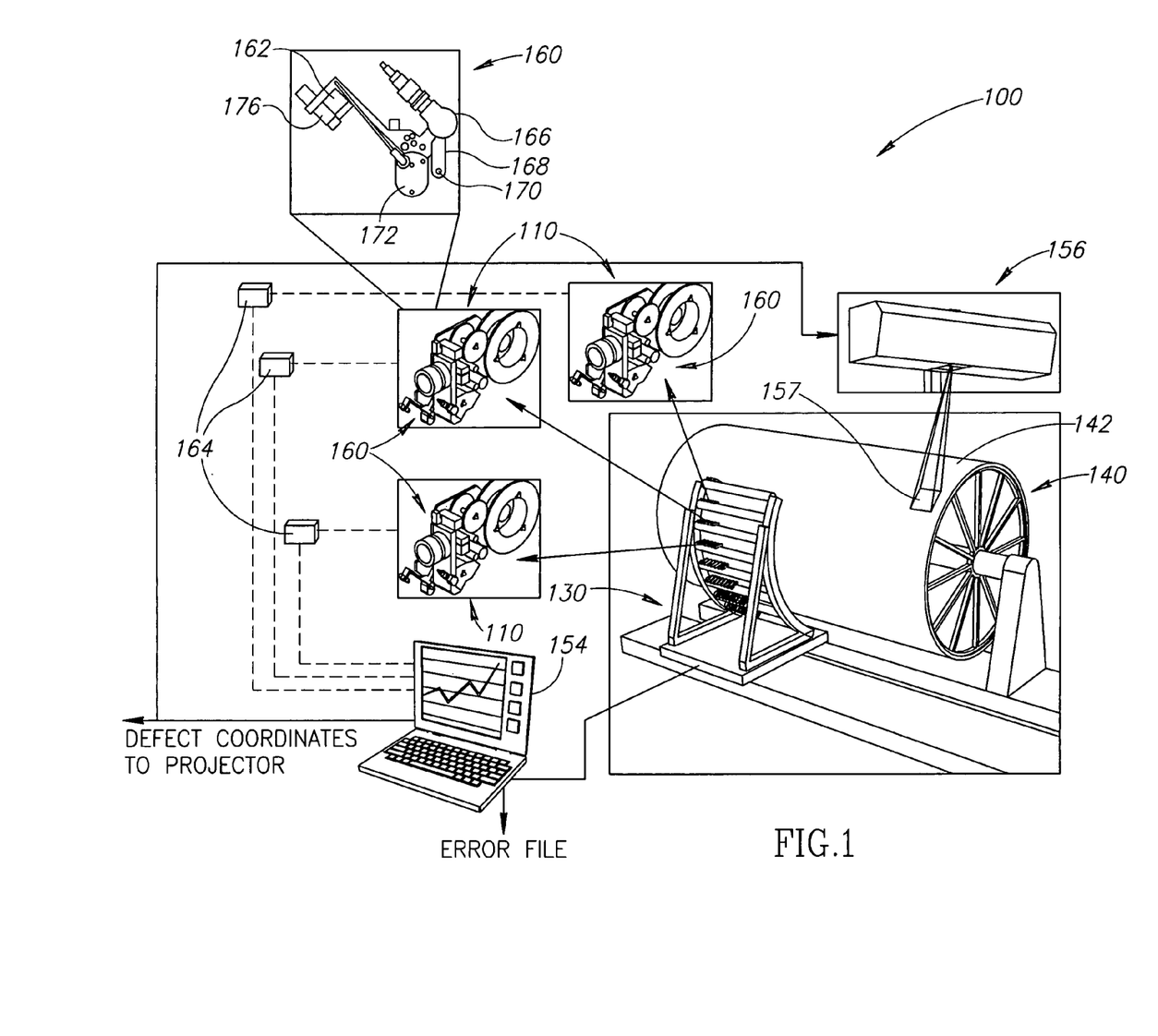
FIG. 1 is an isometric view of a system for manufacturing composite components in accordance with an embodiment of the invention.

FIG. 1 is an isometric view of a system 100 for manufacturing composite components in accordance with an embodiment of the invention. In this embodiment, the system 100 includes a plurality of head assemblies 110 coupled to a translation platform 130 and operatively positioned proximate a forming tool (or template) 140. The translation platform 130 is adapted to systematically move the head assemblies 110 along translation paths (e.g. three-dimensional paths) proximate the forming tool 140, and each head assembly 110 is adapted to perform placement and consolidation of a fiber-reinforced composite tape material onto the forming tool 140 to produce a laminated composite workpiece 142, as described more fully below.

Figure 2:
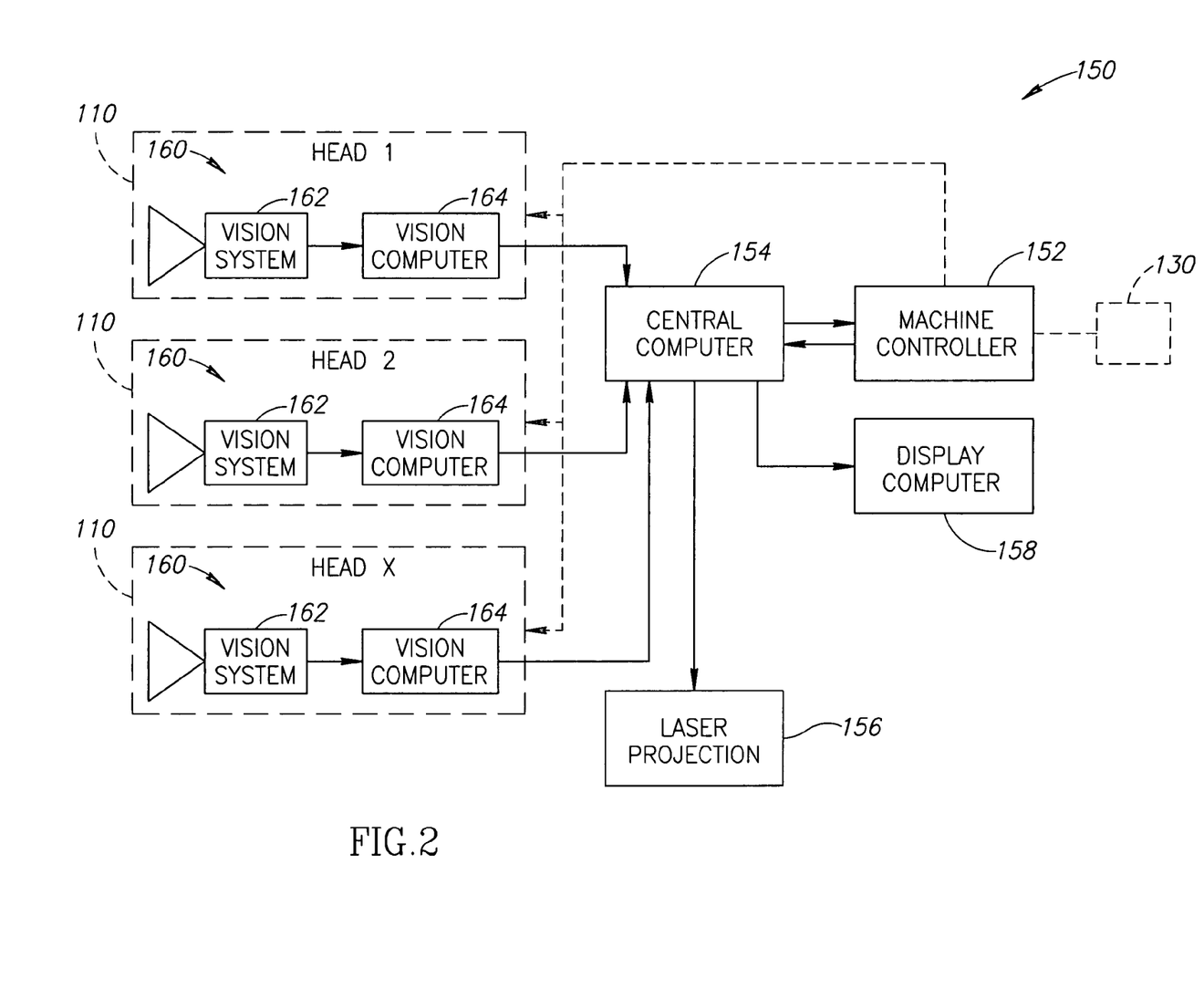
FIG. 2 is a schematic representation of an inspection system of the manufacturing system of FIG. 1.

FIG. 2 is a schematic representation of a control system 150 of the manufacturing system 100 of FIG. 1. In this embodiment, the control system 150 includes a machine controller 152 operatively coupled to the translation platform 130 and to the head assemblies 110. The machine controller 152 is adapted to implement a control code that transmits control signals to the translation platform 130 and the head assemblies 110. The control signals command the movement and functions of the translation platform 130 and the head assemblies 110, thereby causing automated (or semi-automated) manufacturing of the laminated composite workpiece 142 on the forming tool 140. In the embodiment shown in FIG. 1, the manufacturing system 100 is of a type known as a multi-head tape lamination machine (MHTLM). In one specific embodiment, the system 100 includes eight head assemblies 110 for the placement of composite tape, however, in alternate embodiments, any desired number of head assemblies 110 may be employed.

Figure 3:
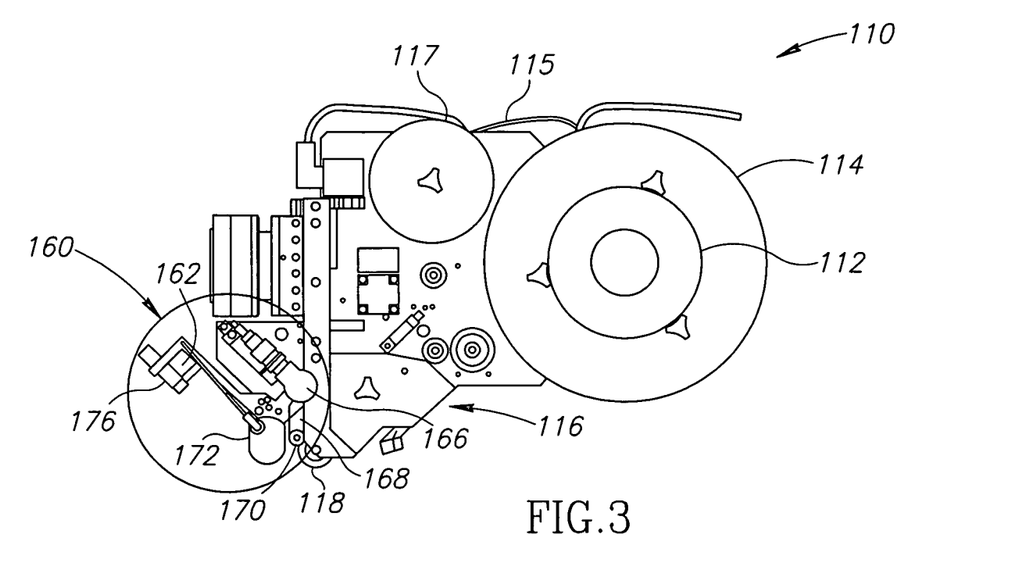
FIG. 3 is a side elevational view of a head assembly of the manufacturing system of FIG. 1.

FIG. 3 is a side elevational view of the head assembly 110 of the manufacturing system 100 of FIG. 1. In this embodiment, the head assembly 110 includes a spindle 112 adapted to retain a roll 114 of a fiber-reinforced composite tape 115, and a feed assembly 116 adapted to receive, guide, feed, and apply the tape 115 from the roll 114 onto the workpiece 142. More specifically, the feed assembly 116 includes a feed roller 117 that receives the tape 115 from the roll 114, and a compaction roller 118 that applies and compresses the tape 115 onto the workpiece 142. The feed assembly 116 may include a variety of other components (e.g. motors, rollers, guides, sensors, etc.) adapted to cooperatively receive, feed, and guide the tape 115 from the roll 114 to the compaction roller 118, as described more fully, for example, in U.S. Pat. No. 6,799,619 B2 issued to Holmes et al., and U.S. Pat. No. 6,871,684 B2 issued to Engelbart et al., as well as in co-pending, commonly-owned U.S. patent application Ser. Nos. 09/998,478 and 10/644,148, which patents and pending patent applications are incorporated herein by reference.

Figure 4:
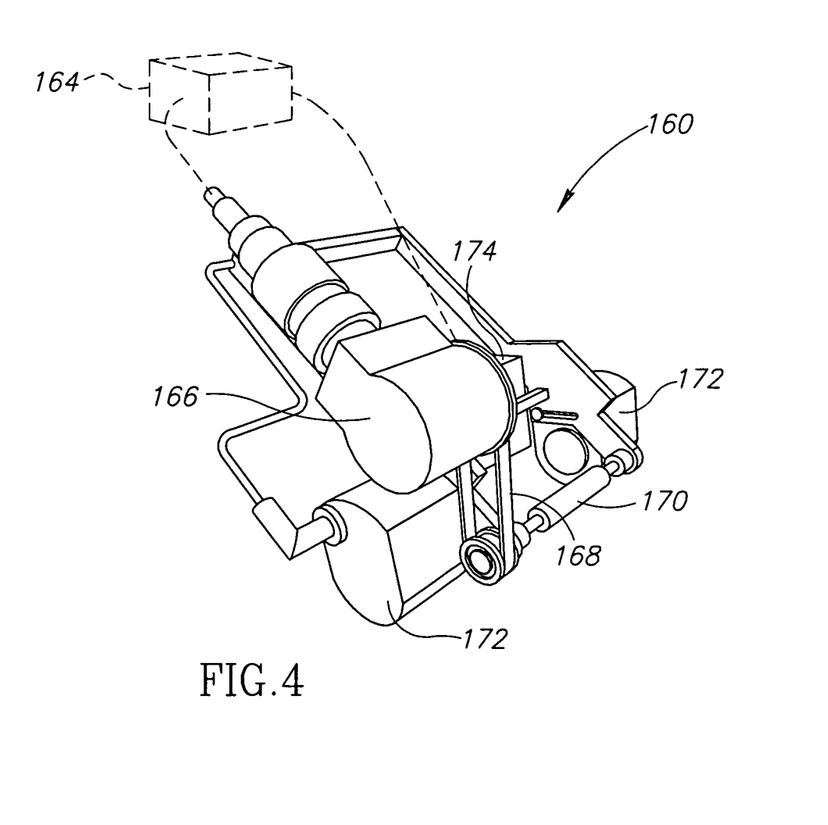
FIG. 4 is an enlarged, isometric view of a vision unit of the manufacturing system of FIG. 1.
Figure 5:
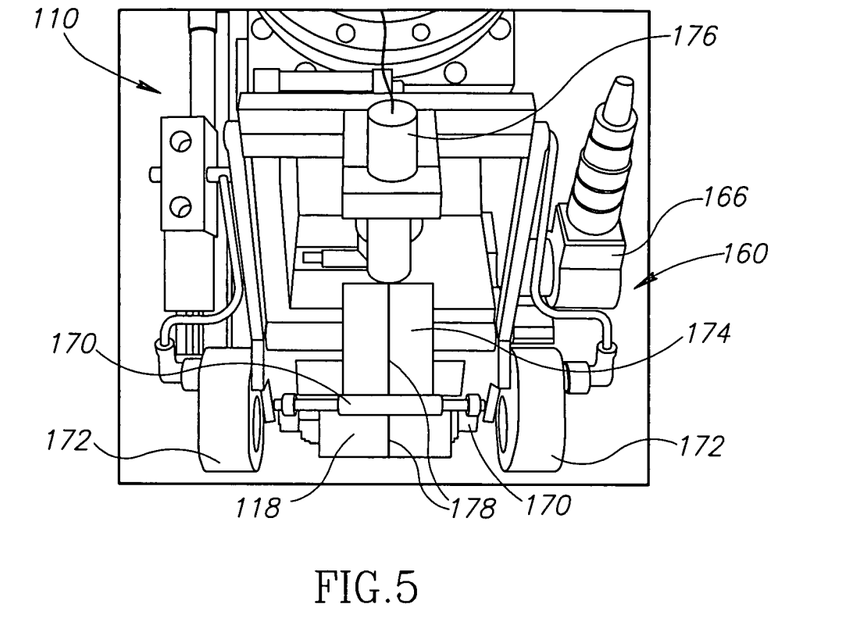
FIG. 5 is a rear elevational view of the vision unit of FIG. 4.
Figure 6:
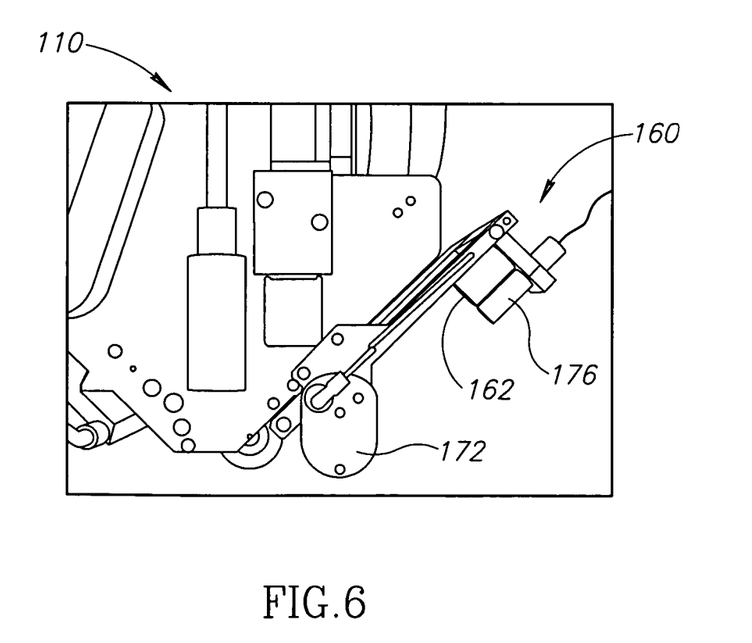
FIG. 6 is a side elevational view of the vision unit of FIG. 4.
Figure 7:
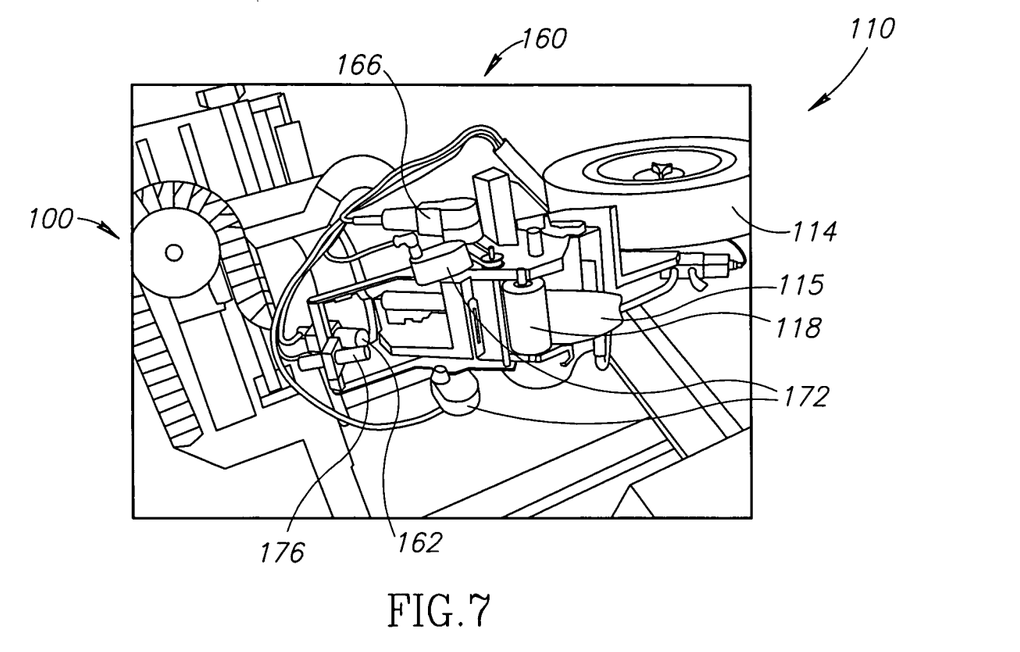
FIG. 7 is a first isometric view of a portion of the manufacturing system including the head assembly of FIG. 3.
Figure 8:
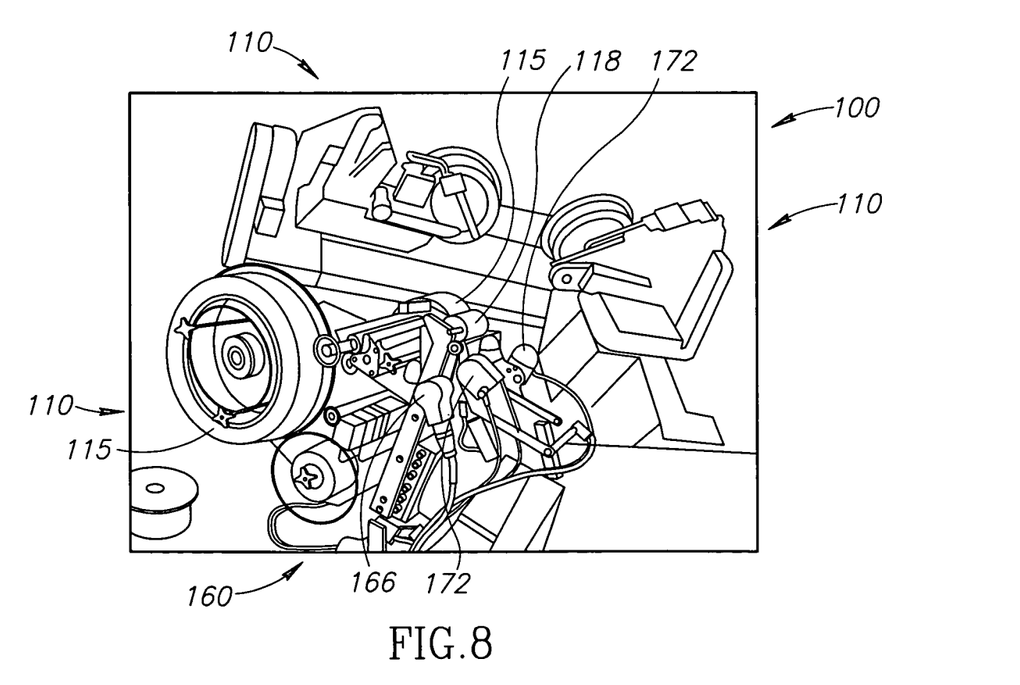
FIG. 8 is a second isometric view of a portion of the manufacturing system including the head assembly of FIG. 3.

The head assembly 110 further includes a vision unit 160 adapted to perform in-process inspections of the manufacturing processes (in this case, composite tape application processes) performed by the head assembly 110. FIG. 4 is an enlarged, isometric view of the vision unit 160 of FIG. 3. FIGS. 5 and 6 are elevational views, and FIGS. 7 and 8 are partial isometric views, of the vision unit 160 coupled to the other portions of the head assembly 110.

As best shown in FIGS. 3 and 6, the vision unit 160 includes a camera 162 operatively positioned to view an area proximate the compaction roller 118 that includes the tape 114 as it is being applied and compressed onto the workpiece 142. A vision computer (or other suitable processor) 164 is coupled to the camera 162 and is adapted to acquire and analyze an image provided by the camera 162 for defects. The vision computer 164 may, for example, be adapted to analyze the image to determine whether any possible defects or errors are present in the image, and make accept/reject decisions based on one or more predetermined criteria stored within the vision computer 164 or otherwise entered through a user interface, as described more fully below.

As shown in FIG. 2, each vision computer 164 is coupled to a central computer 154 which, in turn, is coupled to the machine controller 152. Communication between the vision units 160 and the central computer 154 may be accomplished by standard Ethernet connections, or alternately, by a custom network or server. Communication may also be achieved through a wireless network that utilizes spread spectrum RF to overcome sources of interference in a typical factory environment.

With continued reference to FIGS. 4-8, the vision unit 160 also includes an encoder 166 that is driven by a drive belt 168 coupled to an encoder drive 170. In this embodiment, the encoder drive 170 operatively engages the compaction roller 118 so that as the compaction roller 118 rolls along the workpiece 142, the encoder drive 170 drives the encoder 166 via the drive belt 168. The encoder 166 provides position information to the vision computer 164 for coordinating the location of possible defects indicated by the vision computer 164. As best shown in FIG. 5, two lighting sources 172 are laterally arranged on opposing sides of the encoder drive 170 for illuminating the area proximate the compaction roller 118 that is viewed by the camera 162. A mirror 174 is centrally disposed between the lighting sources 172 and is positioned proximate the compaction roller 118, and a laser 176 is positioned to project a laser line 178 through a portion of the area that is viewed by the camera 162. The mirror 174 may be operatively positioned to enable the camera 162 to simultaneously image the tape 114 that is being placed by the compaction roller 118 as well as to detect change in the laser line 178 projected from the laser 176.

In operation, as the head assemblies 110 are operated to apply the composite tape 115 onto the workpiece 142, the vision computers 164 monitor the application process, analyze the images in real time for possible manufacturing defects, and transmit the results of their image analyses to the central computer 154. As note above, each vision computer 164 may be adapted to analyze the image to determine whether any possible defects or errors are present in the image, and make accept/reject decisions. The vision computer 164 may use a variety of suitable methods and algorithms for determining whether defects or errors are present in the image, and for making the accept/reject decisions, including, for example, those methods and algorithms disclosed in U.S. Pat. No. 6,871,684 issued to Engelbart et al. on Mar. 29, 2005, as well as those methods and algorithms disclosed in the following co-pending, commonly-owned patent applications, incorporated herein by reference: U.S. patent application Ser. No. 09/819,922 by Engelbart et al. filed on Mar. 28, 2001, U.S. patent application Ser. No. 10/628,691 filed on Jul. 28, 2003, U.S. patent application Ser. No. 10/726,099 by Engelbart et al. filed on Dec. 2, 2003, U.S. patent application Ser. No. 10/946,267 by Engelbart et al. filed on Sep. 21, 2004, U.S. patent application Ser. No. 10/904,727 by Engelbart et al. filed on Nov. 24, 2004, and U.S. patent application Ser. No. 10/904,719 by Engelbart et al. filed on Nov. 24, 2004.

In one embodiment, the vision computers 164 transmit analysis results that indicate a possible manufacturing error or defect to the central computer 154, but do not transmit analysis results if no manufacturing errors are indicated.

Figure 10:
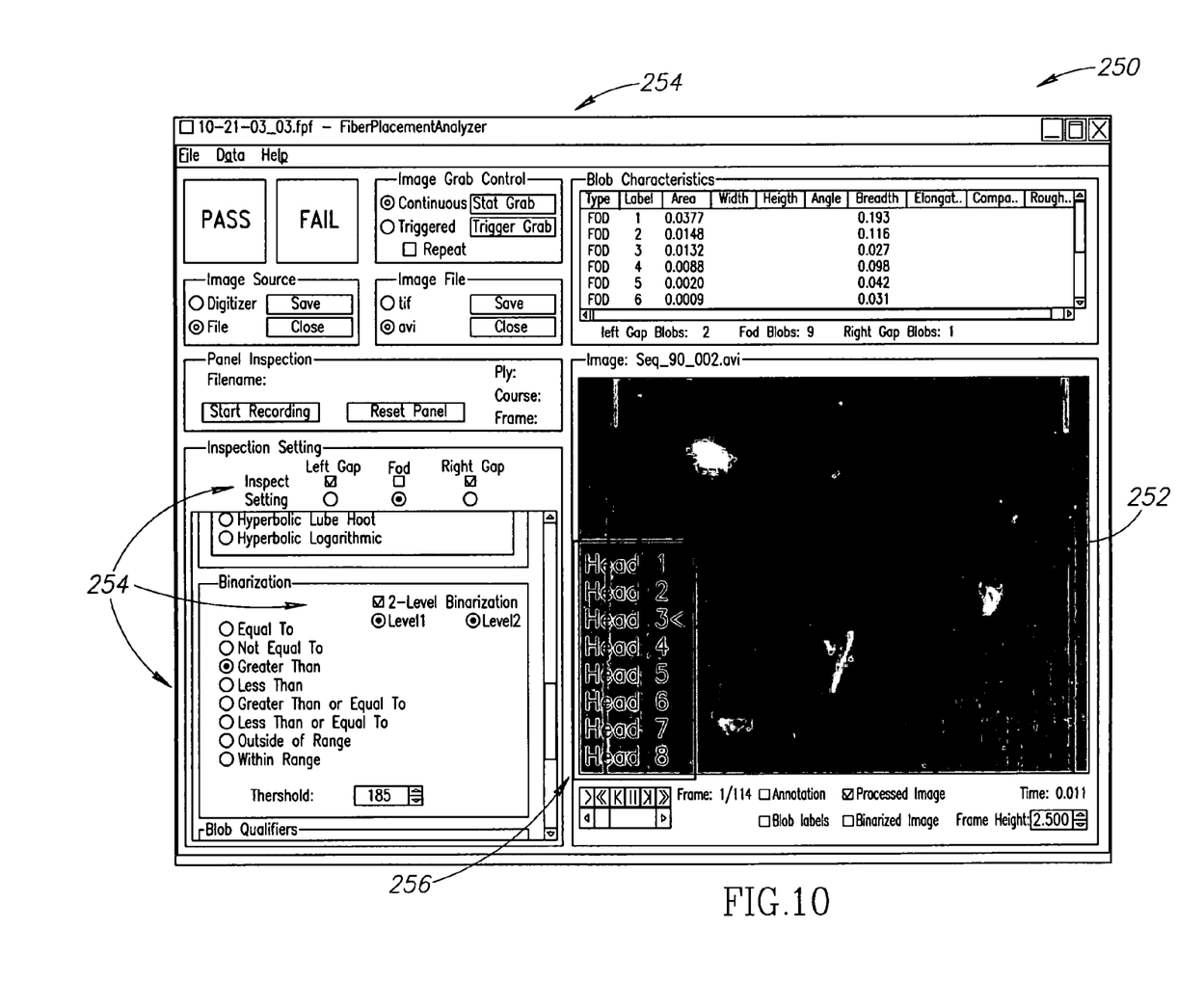
FIG. 10 is a representative image provided by the vision unit of FIG. 4 in accordance with yet another embodiment of the invention.

Alternately, the central computer 154 may receive and maintain a running display of images (both with and without possible defects) as seen through the camera 162 of the vision unit 160. For multiple head assemblies 110, this may be accomplished by a split screen display that shows the view from each head assembly 110 simultaneously in discrete windows. It may also be done by displaying each head assembly 110 view individually through selection of that head assembly 110 from a list (e.g. as shown in FIG. 10).

Upon receipt of defect information, the central computer 154 may query the machine controller 152 for the coordinates (e.g. x-y coordinates) of the possible defect, and may also receive position information from the encoder 166. The central computer 154 may then write the information regarding defects perceived by the vision computers 164 to a system error file 200, and may archive the corresponding images from the vision computers 164.

Figure 9:
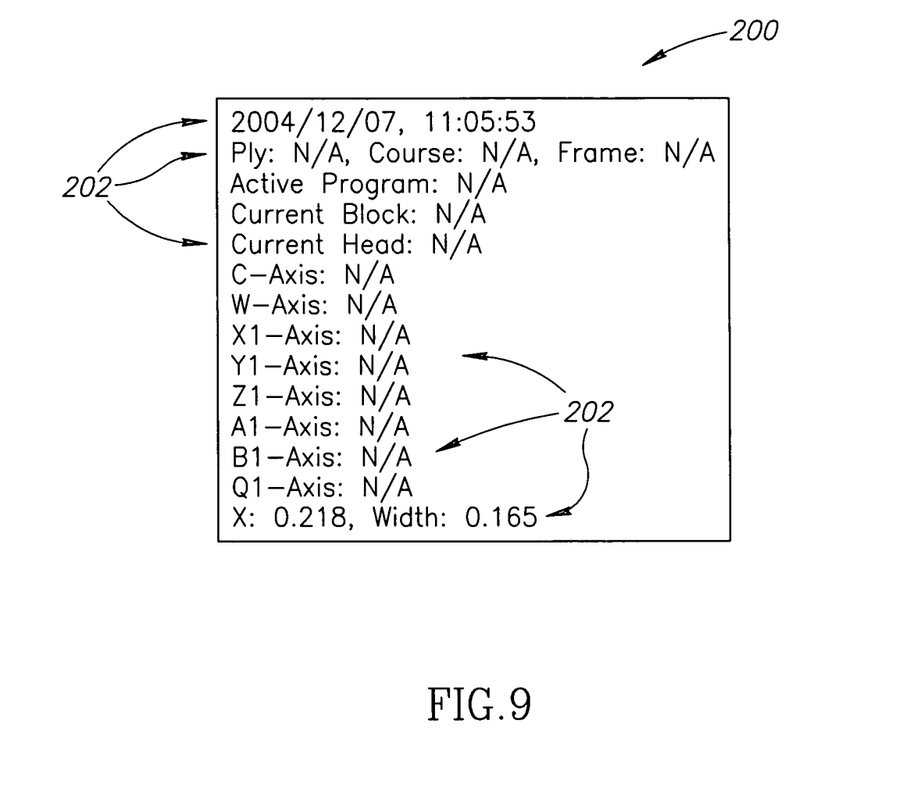
FIG. 9 is a system error file produced by the manufacturing system of FIG. 1 in accordance with an embodiment of the invention.

FIG. 9 is a representative system error file 200 produced by the central computer 154. In this embodiment, the system error file 200 includes a plurality of error file entries 202 which provide various information regarding the possible defect location (e.g. date, time, ply, course, frame, active program, current block, current head, coordinate information from the machine controller 152, position information from the encoder 166, etc.). In one particular embodiment, the central computer 154 maintains a running list of defect locations by machine coordinates, and at the end of each completed ply (or layer), the central computer 154 sends the running list to a laser projection system 156. As shown in FIGS. 1 and 2, the laser projection system 156 may receive the information regarding possible defects from the central computer 154, and may project a defect identifier 157 onto the workpiece 142. The laser projection system 156 may include a processor that converts the machine coordinates for the purpose of locating and marking possible defects for detailed inspection and possible repair. The laser projection system 156 may be any suitable projection system, including those projection systems disclosed, for example, in co-pending, commonly-owned U.S. patent application Ser. No. 10/822,538 filed on Apr. 12, 2004, which application is incorporated herein by reference.

The central computer 154 may also archive the corresponding images from the vision computers 164, as well as the related error file entries 202, and make them available for subsequent viewing and inspection on a display device 158 (FIG. 2). The display device 158 may be driven by the central computer 154, or alternately, a secondary computer may be used to run the display device 158 in order to maintain the processing speed of the central computer 154 for data archiving tasks.

In one embodiment, the images of possible defect locations from the vision computers 164 are provided to the display device 158 by selecting an appropriate error file entry 202 from the error file 200. For example, FIG. 10 is a representative screenshot 250 from the display device 158 that includes an image 252 provided by the vision unit 160 of FIG. 4. The screenshot 250 also includes a plurality of identifying data 254 corresponding to the error file entries 202 which provide information regarding the possible defect location. In this embodiment, a list 256 of head assemblies 110 is provided, allowing the image from each head assembly 110 to be viewed individually by selection of that head assembly 110 (e.g. Head 3) from the list 256.

Figure 11:
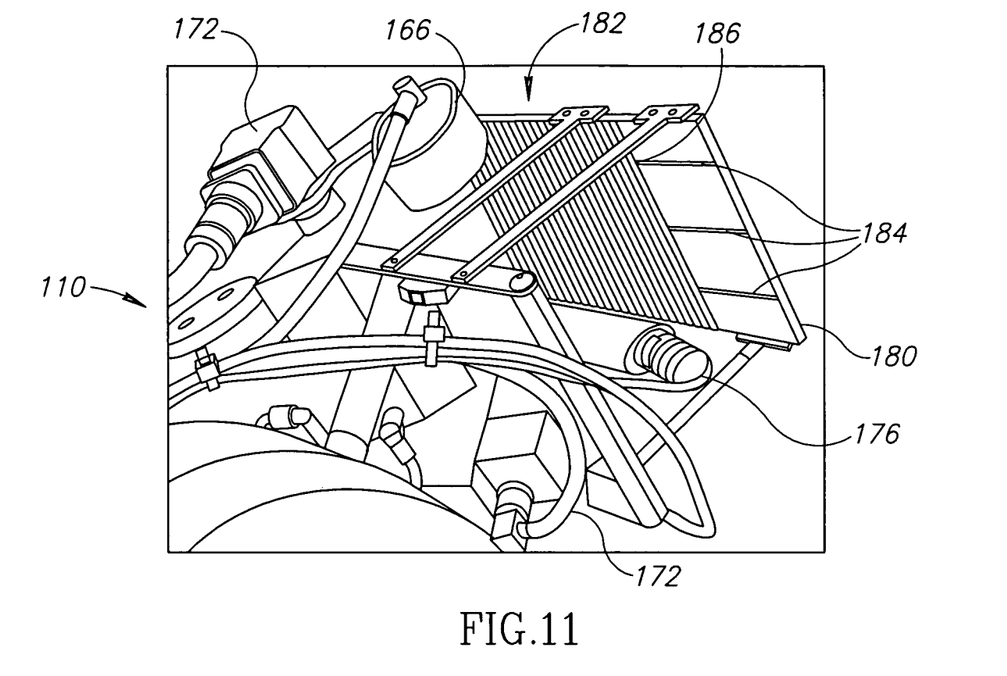
FIGS. 11 and 12 are isometric views of the manufacturing system in first and second modes of operation in conjunction with a calibration plate.
Figure 12:
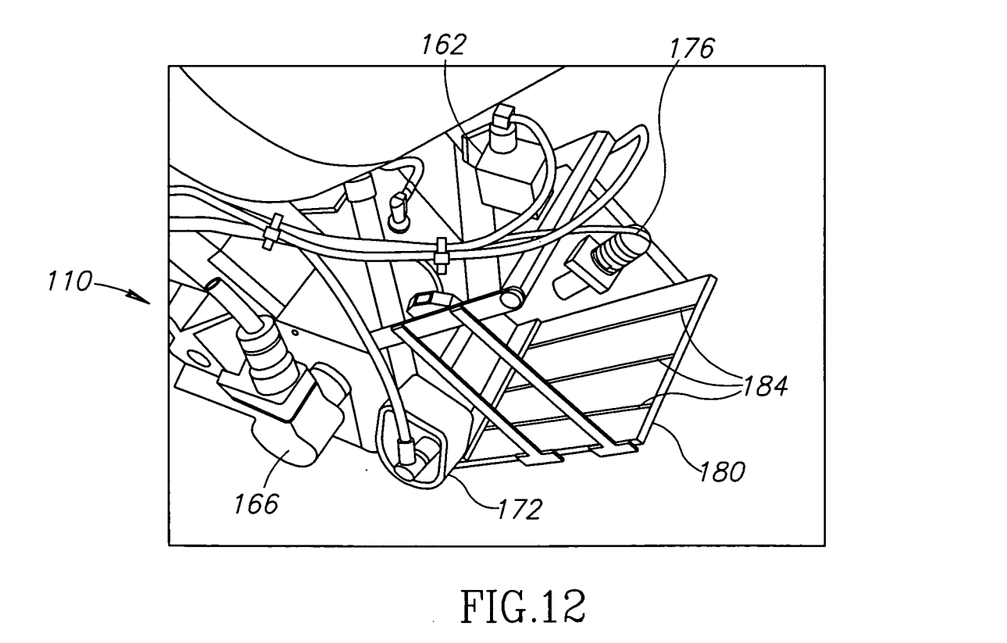
Figure 13:
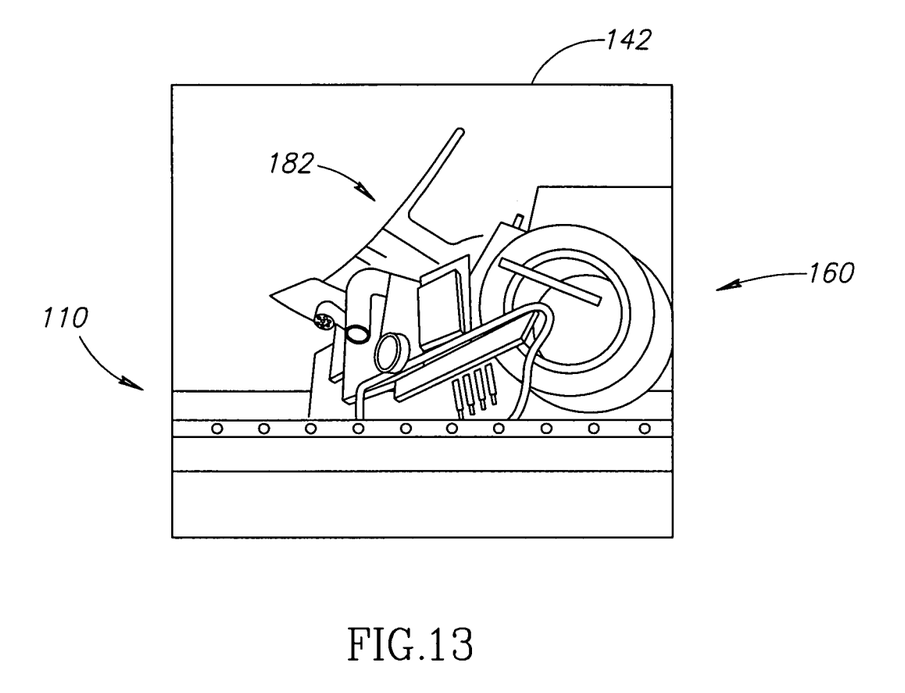
FIG. 13 is an isometric view of the manufacturing system in operation on the workpiece of FIG. 1.
Figure 14:
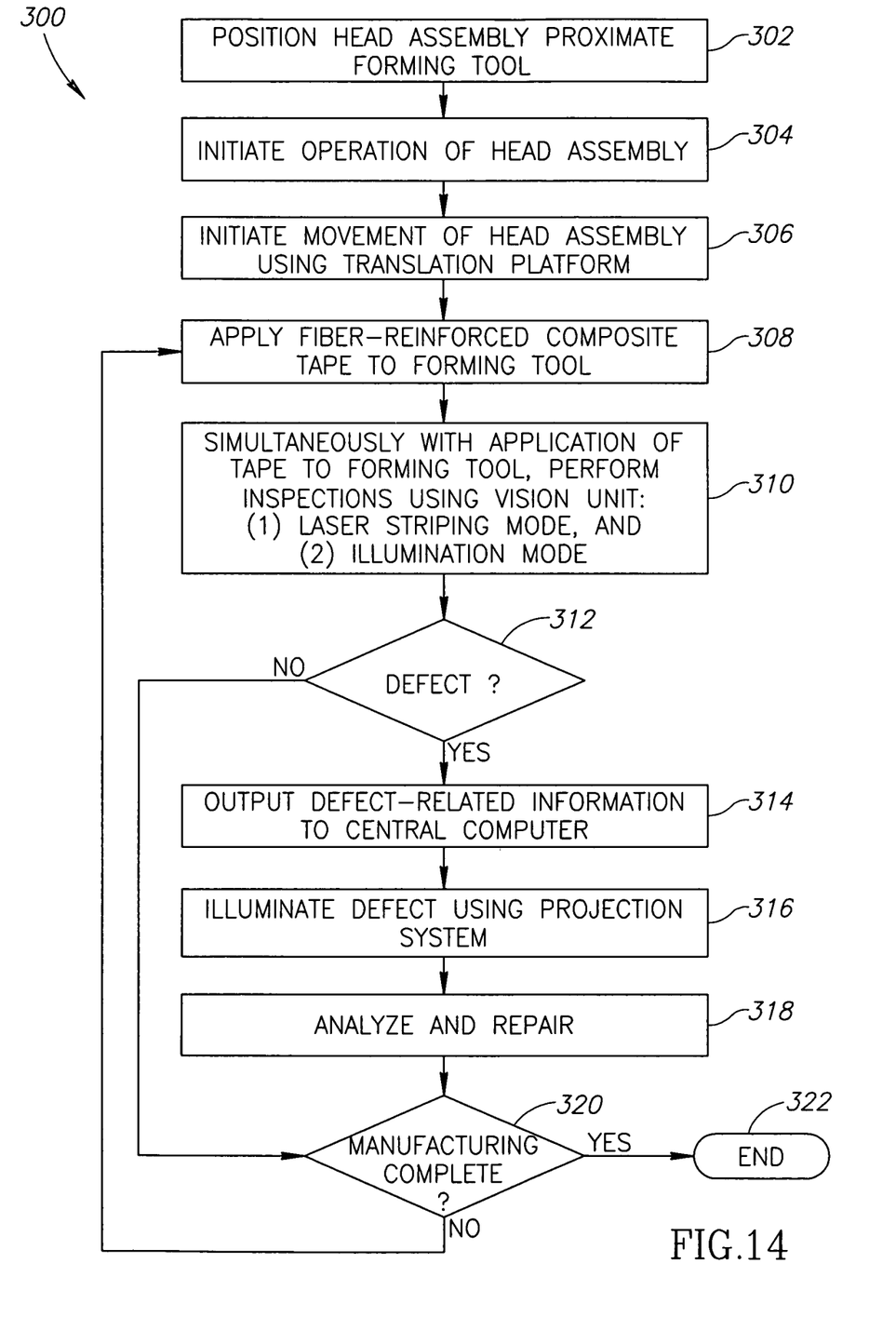
FIG. 14 is a flowchart showing a method of performing manufacturing operations in accordance with an embodiment of the invention.

The overall operation of the manufacturing system 100 will now be described with reference to FIGS. 11 through 14. Specifically, FIGS. 11 and 12 are isometric views of the manufacturing system 100 in operation in conjunction with a calibration plate 180, and FIG. 13 is an isometric view of the manufacturing system 100 in operation on the workpiece 142 (FIG. 1). FIG. 14 is a flowchart showing a method 300 of performing manufacturing operations in accordance with an embodiment of the invention. The method 300 includes positioning the head assembly 110 proximate the forming tool 140 at a block 302, initiating operation of the head assembly 110 at a block 304, and initiating movement of the head assembly 110 using the translation platform 130 at a block 306. At a block 308, the fiber-reinforced composite tape 115 is applied to the forming tool 140 (or to the previously-applied layers of the workpiece 142).

At a block 310, inspections are performed with the vision unit 160 simultaneously with the application of the tape (block 308). More specifically, in a first mode of operation, the vision unit 160 is operated in a laser striping mode to detect gaps between a recently-applied portion of the tape and a previously-applied portion of the tape. As described more fully in the above-referenced issued patents and pending patent applications (previously incorporated by reference herein), in the laser striping mode of operation, the beam from the laser 176 is conditioned by a lens system to form a plurality of lateral stripes 182. As shown in FIG. 11, the lateral stripes 182 are projected onto at least part of the area monitored by the camera 162. In the example shown in FIG. 11, the lateral stripes 182 are projected onto the calibration plate 180, however, during actual manufacturing operations, the lateral stripes 182 are projected onto the workpiece 142, as shown in FIG. 13. A plurality of calibration grooves 184 are formed in the surface of the calibration plate 180 (FIGS. 11 and 12). When the lateral stripes 182 intersect with one of the grooves 184, a discontinuity (or jog, or gap indication) 186 in the lateral stripe 182 becomes apparent. Similarly, on the workpiece 142, gaps which may occur between a recently-applied portion of the tape and a previously-applied portion of the tape also appear as gap indications 186. During actual manufacturing operations, such gap indications 186 are detected by the vision computer 164 during analysis of the images acquired by the camera 162, and corresponding error messages are generated to indicate that a gap has been detected.

Alternately, during the inspections performed using the vision unit 160 (block 310), defects (including foreign objects and debris (FOD)) may be detected using a second or "illumination" mode of operation. Again, as described more fully in the above-referenced issued patents and pending patent applications (previously incorporated by reference herein), in the illumination mode of operation, the lighting sources 172 are activated to brightly illuminate the area monitored by the camera 162. For example, FIG. 12 shows the lighting sources 172 operating in the illumination mode of operation on the calibration plate 180. The vision computer 164 analyzes the resulting images for discontinuities in reflected light intensity, and determines whether defects (e.g. bumps, ripples, irregularities, etc.) are present on the calibration plate 180 (or on the workpiece 142) based on one or more predetermined criteria. The one or more predetermined criteria may, for example, be defined in terms of a presumed area. Any detected discontinuities in reflected light intensity having an area that meets or exceeds the presumed area may be classified as defects, and a corresponding error indicator message may be returned by the vision computer 164.

With continued reference to FIG. 14, at a determination block 312, the method 300 determines whether the inspections performed using the vision unit (block 310) resulted in the detection of a defect. If not, the method 300 proceeds to the determination block 320 to determine whether manufacturing operations are complete. If manufacturing operations are not complete, the method 300 returns to the block 308 and continues the application of the fiber-reinforced composite tape, and the performance of the inspections (block 310), and repeats these operations as needed.

Alternately, if a defect is determined at the block 312, then at a block 314, the defect-related information is output to the central computer 154 (FIG. 2). At a block 316, the projection system 156 may be used to illuminate the area of the possible defect, and at a block 318, the area of the possible defect may be further inspected, analyzed, and repaired if necessary. The method 300 then proceeds to the determination block 320 to determine whether manufacturing operations are complete, and if not, the method 300 returns to the block 308 and continues the application of the fiber-reinforced composite tape, and the performance of the inspections (block 310), and repeats these operations as needed. If manufacturing operations are complete, then the method 300 terminates at the block 322.

Embodiments of systems and methods in accordance with the present invention may provide significant advantages over the prior art. For example, because the head assembly 110 includes its own dedicated vision unit 160 for performing inspections, in-process inspections may be performed simultaneously on different regions of the workpiece 142 as the head assemblies 110 are simultaneously performing manufacturing operations. The vision units 160 advantageously reduce downtime of the manufacturing system 100 by reducing or eliminating the need to shift inspection hardware between head assemblies 110. Also, because the central computer 154 has been relieved of the tasks of image acquisition, image analysis, and decision making by the vision computers 164, the central computer 154 is able to perform other tasks (e.g. archival tasks) relatively more rapidly in order to keep pace with the speed of material placement and inspection by the head assemblies 110.

It will be appreciated that a variety of embodiments in accordance with the present invention may be conceived, and that the invention is not limited to the particular embodiments described above and shown in the accompanying figures. For example, in alternate embodiments, the functions of the central computer 154 and the machine controller 152 (FIG. 2) may be combined into a single computer. Similarly, the display 158 may be integrated with the central computer 154 or with the machine controller 152. Of course, a variety of other embodiments may be conceived by combining various other components.

Furthermore, embodiments of the invention may be used in a wide variety of manufacturing applications for manufacturing a wide variety of components for a wide variety of products. For example, in the manufacturing system 100 shown in FIG. 1, the forming tool 140 is adapted for forming an elongated, tubular workpiece 142. In one specific embodiment, the workpiece 142 is a fuselage portion of an airplane, such as the 787 passenger aircraft commercially-available from The Boeing Company of Chicago, Ill. It will be appreciated, however, that alternate embodiments of the invention may be employed for the manufacture of composite components for a variety of other products, including other components for commercial and military aircraft, rotary wing aircraft, missiles or other types of flight vehicles, as well as components for boats, automobiles, trucks and other types of terrestrial vehicles, and any other desired structures.

Furthermore, although the disclosed embodiments have been described as being adapted for the application and collation of fiber-reinforced composite tape, it may be appreciated that in alternate embodiments, head assemblies having vision inspection units in accordance with the present invention may be equipped with other types of tools for performing other types of manufacturing operations. For example, in alternate embodiments, assemblies in accordance with the invention may include riveters, welders, wrenches, clamps, sanders, nailers, screw guns, mechanical and electromagnetic dent pullers, and virtually any other desired type of manufacturing tools and measuring instruments.

While embodiments of the invention have been illustrated and described above, many changes can be made without departing from the spirit and scope of the invention. Accordingly, the scope of the invention is not limited by the disclosure of these embodiments. Instead, the invention should be determined entirely by reference to the claims that follow.

What is claimed is:

1. A method comprising:
using a tape lamination machine to lay composite tape on a forming tool;
forming lateral stripes on a portion of the tape laid on the forming tool, the lateral stripes extending across a width of the tape laid on the forming tool; and
using a camera to capture images of the lateral stripes; and
processing the images of the stripes to identify any discontinuities in the tape, wherein those stripes intersecting any discontinuities will make those discontinuities apparent.

2. The method of claim 1, wherein a first light source is used to project the stripes onto the portion; the method further comprising processing the images in real time to detect a discontinuity and using a second light source to project a visual defect identifier onto a detected discontinuity in real time as the tape is being applied and compressed on the forming tool, the visual identifier marking the discontinuity for visual inspection during the tape laying.

3. The method of claim 2, further comprising determining coordinates of detected discontinuities on the tape, wherein the coordinates are used to project the visual identifier on the detected discontinuities.

4. The method of claim 1, wherein the stripes are projected from a tape head of the tape lamination machine; and wherein position of the stripes along the forming tool is determined.

5. The method of claim 1, wherein a beam from a laser is conditioned into the lateral stripes, and wherein the stripes are projected onto the tape.

6. The method of claim 1, further comprising illuminating the tape during a second mode of operation, generating images of the illuminated tape, and processing the images to detect any bumps, ripples, irregularities, foreign objects and debris.

7. The method of claim 1, wherein the images are acquired at regular intervals that are triggered by an encoder on a placement head of the tape laying machine.

8. The method of claim 1, further comprising acquiring position coordinates of a defect from the tape laying machine and entering position coordinates of a detected defect into an error log.

9. The method of claim 1, wherein the image processing includes using a computer to analyze the lateral stripes in the images to identify any discontinuities without performing edge analysis.

10. The method of claim 9, wherein multiple placement heads are used to apply and compress the tows, and dedicated image analysis and discontinuity detection are performed for each placement head.

* * * * *